United States Patent [19]

Holy et al.

[11] Patent Number: 5,142,051

[45] Date of Patent: Aug. 25, 1992

[54] N-PHOSPHONYLMETHOXYALKYL DERIVATIVES OF PYRIMIDINE AND PURINE BASES AND A THERAPEUTICAL COMPOSITION THEREFROM WITH ANTIVIRAL ACTIVITY

[75] Inventors: Antonin Holý, Horní Pocernice; Ivan Rosenberg, Praha, both of Czechoslovakia; Erik D. A. De Clercq, Leuven, Belgium

[73] Assignees: Ceskoslovenska Akademie Ved, Praha, Czechoslovakia; Rega Institut, Leuven, Belgium

[21] Appl. No.: 74,900

[22] Filed: Jul. 17, 1987

[30] Foreign Application Priority Data

Jul. 18, 1986 [CS] Czechoslovakia ............ 5469-86

[51] Int. Cl.$^5$ .............. C07F 9/6561; C07F 9/645; A61K 31/675
[52] U.S. Cl. .............. 544/243; 544/244
[58] Field of Search ............ 544/244, 243; 514/81, 514/86

[56] References Cited

U.S. PATENT DOCUMENTS

| 4,287,188 | 9/1981 | Schaeffer | 514/81 |
|---|---|---|---|
| 4,590,269 | 5/1986 | Prisbe et al. | 544/244 |
| 4,659,825 | 4/1987 | Holý et al. | 544/244 |
| 4,670,424 | 6/1987 | MacCoss et al. | 514/81 |
| 4,724,233 | 2/1988 | De Clercq et al. | 514/81 |
| 4,808,716 | 2/1989 | Holý et al. | 544/244 |

FOREIGN PATENT DOCUMENTS

| 84/04748 | 12/1984 | PCT Int'l Appl. | 514/81 |
|---|---|---|---|
| 2134907 | 8/1984 | United Kingdom | 544/244 |

OTHER PUBLICATIONS

Holy, et al., Nucleic Acids Research, Symposium Series No. 14, 1984, pp. 277-278.
De Clercq, et al., Nature, vol. 323, pp. 464-467 (Oct. 2, 1986).

*Primary Examiner*—Diana Rivers
*Attorney, Agent, or Firm*—Leydig, Voit & Mayer

[57] ABSTRACT

This invention relates to new nucleotide analogues and solves the technical problem of their use as biologically active compounds. The subject of this invention are N-(2-phosphonylmethoxyethyl) and N-(3-hydroxy-2-phosphonylmethoxypropyl) derivatives of pyrimidine and purine bases, easily accessible from heterocyclic bases andd their N-(2-hydroxyethyl) or N-(2,3-dihydroxypropyl) derivatives. Some of the compounds, according to this invention, exhibit a marked antiviral activity or can be converted into such active compounds by chemical transformations.

3 Claims, No Drawings

N-PHOSPHONYLMETHOXYALKYL DERIVATIVES OF PYRIMIDINE AND PURINE BASES AND A THERAPEUTICAL COMPOSITION THEREFROM WITH ANTIVIRAL ACTIVITY

This invention relates to N-phosphonylmethoxyalkyl derivatives of pyrimidine and purine bases and a therapeutical composition therefrom with antiviral activity.

Some substituted N-alkyl derivatives of heterocyclic bases exhibit important biological effects. Among them are e.g. theophylline derivatives Diprophyllin ® and Proxyphyllin ® (bronchodilatory effect), guanine derivatives with antiviral activity, such as Zovirax ®, 9-(1,3-dihydroxy-2-propoxymethyl)guanine, (DHPG, nor-2'-deoxyguanosine, BIOLF-62) or 9-(4-hydroxybutyl)guanine (HBG), further adenine derivatives 9-(S)-(2,3-dihydroxypropyl)adenine (DHPA), 3-(adenin-9-yl)-2-hydroxypropanoic acid (AHPA) and its esters, all with antiviral activity (for a review see e.g. M. J. Harnden/Ed/Approaches to Antiviral Agents; Macmillan, London 1985, pp. 101–134). Significant biological effects have been found also for erythro-9-(2-hydroxynonyl)adenine (EHNA), 1-(2-hydroxyethoxymethyl)-5-benzyluracil or 1-(1,3-dihydroxy-2-propoxymethyl)-5-benzyluracil which are specific inhibitors of catabolic enzymes with the possible application in combination chemotherapy of metabolic or malignant diseases.

Most of these compounds can be regarded as so-called acyclic analogues of nucleosides in which the nucleoside sugar moiety is replaced by a substituted carbon chain bearing hydroxy groups. In the organism, the biologically active nucleoside analogues with chemically modified heterocyclic bases or sugar moieties are usually phosphorylated to give 5'-monophosphates which then act as so-called active antimetabolites. However, attempted therapeutical applications of such compounds were not particularly successful: although in some cases the physical and pharmacological parameters (solubility, higher absorption, prolonged activity etc.) have been improved as compared with those of the corresponding nucleoside analogues, the main obstacle to the therapeutical use of the phosphoric acid esters remains their facile dephosphorylation in the organism. This disadvantage can be overcome by a suitable chemical modification of the phosphoric acid-nucleoside bond. However, compounds of this type described so far have not been therapeutically useful.

On the other hand, it is known that 9-(ω-phosphonylalkyl)hypoxanthines inhibit purine nucleoside phosphorylase—an important target enzyme in the therapy of metabolic and malignant diseases (C. E. Nakamura, S. H. Chu, J. D. Stoeckler and R. E. Parks Jr.: Biochem. Pharmacol. 35, 133–136 (1986)). Also an antiviral effect of 9-(phosphonylalkoxymethyl)purines has been reported (U.S. patent application No. 497,720 (1983)). This group of compounds which is characterized by a modified phosphoric acid residue comprizes also two extraordinarily important acyclic nucleotide analogues: 9-(S)-(2-phosphonylmethoxy-3-hydroxypropyl)adenine (HPMPA) (Czechoslovak Author's Certificate 233665) and 9-(2-phosphonylmethoxyethyl)adenine (PMEA)(PV-3017-85). Both these compounds are very potent antivirals, acting specifically against DNA viruses (PV-3018-85). Viruses of this group, e.g. herpes viruses (herpes simplex, herpes zoster, cytomegalo viruses, Epstein-Barr virus), pox viruses and adenoviruses, can inflict serious diseases. Some of these diseases have so far been treated with the above-mentioned antivirals (Zovirax ®, DHPG; D. S. Freestone: Antiviral Res. 15, 307–324 (1985)). Application of these drugs is limited not only by their low water-solubility and side-effects but mainly by the dependence of their effect on the presence of a specific viral enzyme, thymidine kinase. Those strains or mutants of the above viruses that are devoid of this enzyme are not sensitive to the antivirals mentioned. These strains are usually also resistant toward modified nucleoside antivirals, e.g. 5-(2-bromovinyl)-2'-deoxyuridine.

The acyclic nucleotide analogues HPMPA and PMEA are effective even in those cases where the above-mentioned drugs fail.

This invention is based on the new and unexpected finding that the antiviral effect of acyclic nucleotide analogues is not limited to the adenine derivatives HPMPA and PMEA only. The invention relates to new N-phosphonylmethoxyalkyl derivatives of pyrimidine and purine bases of the general formula I

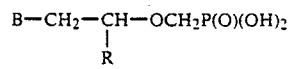

wherein R is a hydrogen atom or a hydroxymethyl group and B is a pyrimidin-1-yl, pyrimidin-3-yl, purin-3-yl, purin-7-yl or purin-9-yl residue but not an adenin-9-yl residue, and the salts thereof with alkali metals, ammonia or amines.

This invention relates further to the therapeutical composition exhibiting antiviral activity, containing compound of the general formula I as active ingredient in a concentration from 0.01 wt % to 100 wt %.

The antiviral effect of compounds of the general formula I can be utilized for the therapy of viral diseases, e.g. diseases caused by DNA viruses. An important property of compounds of the general formula I is their antiviral effect against those DNA viruses which are resistant to the hitherto known antivirals, e.g. against TK⁻ mutants of herpes viruses. Contrary to the hitherto known antiviral nucleoside analogues, derived usually from a single heterocyclic base (Zovirax, DHPG and HBG are guanine derivatives, whereas DHPA, AHPA and Vidarabin are derived from adenine) the antiviral effect of compounds of the general formula I is not limited to a specific heterocyclic base. This fact indicates a completely different mechanism of action of compounds of the general formula I which is supported also by their effect against strains and mutants resistant to other antivirals. In addition to the already mentioned adenine derivatives (HPMPA, PMEA), also the chemically substantially different cytosine and guanine derivatives of the formula I are highly effective against TK⁻ mutants of herpes viruses type 1 and 2 as well as against vaccinia virus. Moreover, the cytosine compounds of the general formula I may be more easily accessible than the adenine derivatives (HPMA, PMEA).

The therapeutical compositions according to this invention containing as active ingredient compounds of general formula I can be applied in the form of powders, suspensions, solutions, sprays, emulsions, pastes, ointments, etc. and can be used for parenteral administrations (intravenous, intradermal, intramuscular, intrathecal, etc.) as well as for oral, rectal, intravaginal or intranasal administration or topical applications. Such compositions can be prepared by mixing or dissolving the salt or the free acid of the compound of the general formula I with pharmaceutically acceptable carriers, stabilizers, solvents, wetting agents, additives etc. used for such purposes. According to the requirements and application form, these preparations can contain various concentrations of the compounds of the formula I, from 0,1% up to 100 wt %.

Compounds of the general formula I, where R is an atom of hydrogen (i.e. 2-phosphonylmethoxyethyl derivatives of heterocyclic bases) can be prepared in analogy to the procedure elaborated for PMEA (PV-3017-85), i.e. by reaction of N-(2-hydroxyethyl) derivative of the corresponding heterocyclic base of the general formula II

B—CH$_2$CH$_2$OH  (II)

wherein B has the same signification as in the formula I, with diesters of p-toluenesulfonyloxymethanephosphonic acid and subsequent reaction with trimethylhalogenosilanes, or by reaction of an alkali metal salt of the heterocyclic base with diesters of 2-bromoethoxymethanephosphonic acid of the general formula III BrCH$_2$CH$_2$OCH$_2$P(O)(OC$_2$H$_5$)$_2$  (III)

to give intermediate of the general formula IV

B—CH$_2$CH$_2$OCH$_2$P(O)(OC$_2$H$_5$)$_2$  (IV)

wherein B signifies the same as in formula I, followed by treatment with trimethylhalogenosilanes.

Compounds of the general formula I, where R is a hydroxymethyl group, i.e. N-(3-hydroxy-2-phosphonylmethoxypropyl) derivatives of heterocyclic bases, contain one asymmetric carbon atom. Both the enantiomeric forms as well as the racemates can be prepared from N-(2,3-dihydroxypropyl) derivatives of heterocyclic bases of the general formula V

B—CH$_2$CH(OH)CH$_2$OH  (V)

accessible from the corresponding heterocyclic bases by a number of synthetic procedures (A. Holý: Collect. Czechoslov. Chem. Commun. 40, 187 (1975); ibid 43, 3103 (1978)). They can be converted into compounds of the formula I by reaction of specifically protected derivatives of compounds of the formula V, containing free 2-hydroxy group, with the mentioned diesters of p-toluenesulfonyloxymethanephosphonic acid and subsequent cleavage with trimethylhalogenosilanes (Czechoslovak Patent Application PV 3017-85). A more advantageous procedure, however, consists in the reaction of unprotected compounds of the formula V with chloromethanephosphonyl dichloride of the formula VI ClCH$_2$P(O)Cl$_2$  (VI)

either in pyridine (Czechoslovak Author's Certificate 233665) or to advantage in triethyl phosphate, and subsequent isomerization of the formed 2'-O-chloromethanephosphonyl esters of the compounds V to the 3'-O-chloromethanephosphonyl esters of the general formula VII B—CH$_2$CH—CH$_2$OP(O)(OH)CH$_2$Cl  (VII)
         |
         OH wherein B has the same signification as in the formula I, in a mineral acid or water. Treatment of compounds of the formula VII with aqueous alkali metal hydroxides according to Czechoslovak Author's Certificate 233665 affords compounds of the formula I (R is hydroxymethyl group) in practically quantitative yields.

Further compounds of the general formula I can be prepared by chemical transformations of the heterocyclic base: thus, e.g. the reaction of uracil derivatives (I, B is uracil-1-yl) with bromine or iodine affords compounds of the formula I, wherein B is 5-halogenouracil-1-yl, treatment of adenine derivatives (HPMPA, PMEA) with nitrous acid or amyl nitrite leads to compounds of the formula I, wherein B is a hypoxanthin-9-yl moiety, and a similar deamination of guanine derivatives gives compounds I wherein B is a xanthin-9-yl moiety. Also substitution at the purine base, e.g. with chlorine, in the pre-formed skeleton of compounds of the general formula I leads to the corresponding N-phosphonylmethoxyalkyl-8-halogenopurines. On the other hand, compounds of the general formula I, wherein B is a 2-methylthioadenin-9-yl, can be transformed into HPMPA or PMEA by desulfuration reaction, e.g. with Raney nickel.

The transformation of the heterocyclic ring can be utilized particularly in such cases when the reaction conditions in the preparation of compounds of the formula I from the heterocyclic base do not afford the desired isomer (hypoxanthine, xanthine) or lead to destruction of the heterocyclic base (mainly due to the use of strong alkali in the reaction of the intermediate of the formula VII). Halogeno derivatives of the pyrimidine or purine series can also serve as the starting compounds for further transformations of the heterocyclic base.

The heterocyclic base in compounds of the general formula I may be not only a so-called natural pyrimidine or purine base (uracil, thymine, cytosine, guanine, adenine, hypoxanthine, xanthine) or its substituted derivative, but also a modified base such as an aza, deaza, deoxy or deamino analogue, a 6-alkylpurine, etc.

N-Phosphonylmethoxyalkyl derivatives of the general formula I are acids of medium strength. They can be easily purified by chromatography on anion exchange resins (such as Dowex 1, Sephadex A-25, DEAE cellulose etc.), preferably in volatile organic acids, (e.g. acetic acid or formic acid) or in volatile neutral buffers (e.g. triethylammonium hydrogen carbonate). Some of the compounds according to the invention (particularly those with basic heterocyclic moieties) can be stored as free acids which, however, may be sparingly soluble in water. Higher solubility is achieved by conversion of the free acids into their well-soluble salts, particularly alkali metal salts (sodium, lithium), by neutralization or (from the acids or other salts) by ion-exchange. The compounds of the general formula I can be easily characterized by their ultraviolet spectra, paper chromatography, high performance liquid chromatography or paper electrophoresis; at the same time, these methods serve as homogeneity criteria.

The antiviral activity of compounds of the general formula I is determined by measurement of inhibitory effect on virus-induced cytopathogenicity their e.g. on the PRK-cells (primary rabbit kidney cells) in tissue cultures previously infected with the corresponding virus and then cultivated in a medium containing various concentrations of the compounds of the general formula I. The compound is regarded as significantly active if an effect is observed at a concentration not exceeding 100 µg. ml$^{-1}$ of medium without changing markedly the cell morphology in the control (virus-uninfected) culture of the same cells under the same conditions.

A survey of the effect of compounds of the formula I on some representative viruses is given in Table 1, the preparation of the compounds is described in the Examples, and their characteristics are given in Table 2, without limiting in any way either the structure of the compounds or their antiviral effects.

EXAMPLE 1

Determination of Antiviral Activity of Compounds of the General Formula I in Cell Culture Confluent monolayers of primary rabbit kidney cell cultures (PRK-cells) in microtiker tray wells in Engl minimum essential medium (EMEM) are inoculated with the virus (100 CCID$_{50}$; 1 CCID$_{50}$ represents the amount of the virus required for infection of 50% cells under the given conditions) for 1 hour. Then the virus solution is removed, the culture is washed with the basic medium and cultivated in solutions of EMEM containing various concentration (wt/vol) of compounds of the formula I. The cytopathogenic effect of the virus in these cultures is evaluated at the time of achieving 100% in the control, infected culture, cultivated in the medium alone. The antiviral effect is expressed as MIC$_{50}$ (µg. ml$^{-1}$) (minimum concentration of compound of the formula I which reduces the cytopathogenic effect of the virus to 50%) and is obtained from a series of measurements at various concentration of compounds I. The antiviral activities of compounds of the general formula I are given in Table 1.

EXAMPLE 2

Preparation of Compounds of the General Formula I (R=H)

A solution of diethyl 2-bromoethoxymethanephosphonate (2.75 g; 10 mmol) in dimethylformamide (10 ml) is added dropwise at 80° C. during 2-3 hours under exclusion of moisture to a stirred solution of sodium salt of the heterocyclic base, (prepared from 10 mmol of the base and 0.24 g (10 mmol) of sodium hydride in 80 ml of dimethylformamide). After stirring at 80° C. for 3-5 hours, the solvent is evaporated at 13 Pa and the residue is extracted with boiling chloroform (400-500 ml). The extract is concentrated in vacuo and chromatographed on a column of silica gel (200 ml) in ethanol-chloroform (gradient elution), affording chromatographically homogeneous compound IV which can be crystallized from a mixture of ethyl acetate (or ethanol) and light petroleum. This product is treated with trimethylbromosilane (2.4 ml) in acetonitrile (40 ml) for 16 hours at room temperature. The solvent is evaporated at 2 kPa, the residue is dissolved in 10% triethylamine solution in 50% (vol/vol) aqueous acetonitrile and after 30 min the solvent is again evaporated at 2 kPa. The residue is chromatographed on a column of Sephadex A-25 (HCO$_3^-$; 150 ml) with a linear gradient (2 liters total) of 0.02–0.2 mol.l$^{-1}$ triethylammonium hydrogen carbonate, pH 7.5. The main UV-absorbing fraction containing the compound I is taken down and the buffer is removed by repeated co-distillation with methanol (all the evaporations are done at 2 kPa), the residue is dissolved in water (20 ml) and applied on to a column of Dowex 50×8 (Na$^+$; 50 ml) and eluted with water. The UV-absorbing eluate is taken down and the product is precipitated from methanol with ether. The sodium salt of compound I (R=H) thus obtained is isolated in 80–90% yield (from V).

Compounds of the general formula I prepared in this manner are listed in Table 2.

EXAMPLE 3

Preparation of Compounds of the General Formula I (R=H)

The reaction is carried out with 10 mmol of the heterocyclic base as described in Example 2. Dimethylformamide is evaporated at 13 Pa and instead of extraction with chloroform, the intermediate IV is heated with 1 mol.l$^{-1}$ sodium hydroxide (50 ml) to 80° C. for 8 hours. After neutralization with a cation exchange resin (H$^+$-form), the mixture is made alkaline with triethylamine, filtered, taken down at 2 kPa, and the residue is dried at 13 Pa over phosphorus pentoxide. The reaction with trimethylbromosilane and the work-up procedure are carried out as described in Example 2.

Compounds of the general formula I, prepared in this way, are listed in Table 2.

EXAMPLE 4

Preparation of Compounds of the General Formula I (R=CH$_2$OH)

Chloromethanephosphonyl dichloride (0.40 ml) is added to a stirred mixture of the N-(2,3-dihydroxypropyl) derivative V and triethyl phosphate (10 ml). After stirring for 16 hours in a stoppered flask, ether (80 ml) is added and the formed precipitate is filtered, washed with ether and dried at 13 Pa. A solution of this material in water (20 ml) is refluxed for 8 hours, neutralized with triethylamine and the solvent is evaporated at 2 kPa. The residue is dissolved in water (1.5 ml) and 0.3 ml portions of this solution are applied on to a column (8×500 mm) of octadecyl-silica gel (e.g. Separon SIX C18, 7µ), equilibrated with 0.05 mol.l$^{-1}$ triethylammonium hydrogen carbonate, pH 7.5. The column is washed with the same buffer until the salts are removed and then with a step-wise gradient of methanol in the same buffer (usually to 10 vol %), elution rate 2 ml.min$^{-1}$. The combined eluates, containing compound VII, are stripped of solvent at 2 kPa and heated with 2 mol.l$^{-1}$ sodium hydroxide (10 ml) to 80° C. The mixture is neutralized with a cation-exchanger (in H$^+$ form), filtered and the solvent is removed at 2 kPa. The further processing is the same as described in Example 2 and affords sodium salt of compound I (R=CH$_2$OH) in 50–60% yield (from compound V).

Compounds of the formula I prepared in this manner are listed in Table 2.

EXAMPLE 5

Preparation of Compounds of the General Formula I (R=CH$_2$OH)

The reaction is carried out as described in Example 4. After boiling the reaction intermediate in the aqueous solution, the content of compound VII is determined by HPLC (usually more than 80% of the isomer mixture). The mixture is neutralized with sodium hydroxide, taken down at 2 kPa and the residue is heated to 80° C. with 2 mol.l$^{-1}$ sodium hydroxide (20 ml) for 10 hours. The solution is neutralized with a cation-exchange resin (H$^+$ form), made alkaline with triethylamine, filtered and evaporated at 2 kPa. The crude product is purified by chromatography on Sephadex A-25 as described in Example 2, affording the sodium salt of compound I (R=CH$_2$OH) which contains more than 80% of this isomer.

EXAMPLE 6

To a solution of sodium salt of 9-(2-phosphonylmethoxyethyl)adenine (4 mmol) in 80% acetic acid (50 ml) is added 3-methylbutyl nitrite (4 ml). After standing in a stoppered flask for 72 hours at room temperature, the solvent is evaporated at 2 kPa and the residue repeatedly codistilled with water to remove traces of acetic acid. The residue is dissolved in water (10 ml), applied on to a column (200 ml) of a cation-exchange resin (e.g. Dowex 50×8) (H$^+$ form) and eluted with water to drop of UV absorption. This eluate is evaporated at 2 kPa, the residue is codistilled with ethanol, crystallized from ethanol - ether (10 ml: 50 ml), filtered, washed with ether and dried at 13 Pa. Yield 0.93 g (90%) of 9-(2-phosphonylmethoxyethyl)hypoxanthine (free acid), not melting up to 260° C.

EXAMPLE 7

Bromine (0.5 ml) is added to a stirred solution of sodium salt of 9-(S)-(3-hydroxy-2-phosphonylmethoxypropyl)adenine (2 mmol) in 1 mol.l$^{-1}$ sodium acetate, pH 4.0 (40 ml). After stirring at room temperature for 2 days, the mixture is decolorized with saturated solution of sodium hydrogen sulfite and the whole solution is applied on to a column of a cation-exchange resin (e.g. Dowex 50×8) (H$^+$ form; 150 ml). After washing the column with water to drop of conductivity and UV absorption, the product is eluted with 2% (vol) aqueous ammonia. The ammonia UV-absorbing eluate is evaporated at 2 kPa and the residue in water is filtered through a column of octadecyl-silica gel (80 ml). The UV-absorbing eluate is again evaporated at 2 kPa, dissolved in water (5 ml) and applied on to a column of Dowex 50×8 (Na$^+$ form; 50 ml). The column is washed with water, the UV-absorbing eluate is taken down at 2 kPa, the residue is codistilled with ethanol, mixed with ethanol (10 ml) and ether (100 ml) and collected on filter. Yield 55% of sodium salt of 9-(S)-(3-hydroxy-2-phosphonylmethoxypropyl)-8-bromoadenine which (according to HPLC analysis) contains less than 0.5% of the starting compound.

EXAMPLE 8

Sodium salt of 9-(RS)-(3-hydroxy-2-phosphonylmethoxypropyl)-2-methylthioadenine (2.0 g) is added to moist Raney nickel (7 g) in 0.2 mol.l$^{-1}$ sodium hydroxide (25 ml). After stirring under reflux for 72 hours, the hot mixture is filtered through Celite which is then washed with boiling water (100 ml) and the filtrate is neutralized with a cation-exchanger (H$^+$ form). According to HPLC analysis, the product contains 75–80% of the reaction product. After evaporation, the residue is dissolved in water (10 ml) and applied on to a column of octadecyl-silica gel (20μ, 180 ml) in 0.05 mol.l$^{-1}$ triethylammonium hydrogen carbonate, pH 7.5. The product is eluted with the same buffer, elution rate 1 ml.min$^{-1}$, fractions 20 ml, monitored by HPLC (see Table 2). The product-containing fractions are combined, evaporated at 2 kPa and the product is converted into the sodium salt of (RS)-HPMPA as described in Example 2; yield 65–70%.

TABLE 1

Antiviral effect of compounds of the general formula I on primary rabbit kidney cell cultures (MIC$_{50}$, μg·ml$^{-1}$)

| B | R | MCC$_{50}$ | HSV-1 (KOS) | HSV-1 (F) | HSV-1 (McIntyre) | HSV-2 (G) | HSV-2 (196) | HSV-2 (Lyons) | HSV-1 TK$^-$ (Cheng) | HSV-1 TK$^-$ (Field) | VV |
|---|---|---|---|---|---|---|---|---|---|---|---|
| Thymin-1-yl | (S)—CH$_2$OH | 400 | 70 | 150 | 70 | 20 | 150 | 70 | 400 | 200 | 300 |
| Cytosin-1-yl | (S)—CH$_2$OH | 100 | 7 | 2 | 1 | 20 | 2 | 20 | 10 | 7 | 0,2 |
| 2-Aminoadenin-9-yl | (S)—CH$_2$OH | 200 | 20 | 7 | 2 | 4 | 7 | 7 | 7 | 7 | 0,7 |
| 6-Hydrazino-purin-9-yl | (RS)—CH$_2$OH | 400 | 150 | 70 | 70 | 70 | 70 | 70 | 70 | 40 | 20 |
| 6-Hydroxylamino-purin-9-yl | (RS)—CH$_2$OH | 400 | 20 | 20 | 7 | 20 | 20 | 20 | 20 | 7 | 7 |
| Guanin-9-yl | (RS)—CH$_2$OH | 400 | 20 | 7 | 2 | 20 | 20 | 20 | 7 | 10 | 2 |
| 2-Aminoadenin-9-yl | H | 200 | 7 | 2 | 2 | 2 | 2 | 2 | 7 | 7 | 70 |
| 2-Aminopurin-9-yl | H | 200 | 70 | 70 | 70 | 20 | 20 | 7 | 150 | 150 | 200 |
| Guanin-9-yl | H | 40 | 7 | 2 | 2 | 4 | 2 | 7 | 7 | 7 | 7 |
| 3-Deazaadenin-9-yl | (S)—CH$_2$OH | 40 | 0,2 | 0,2 | 0,7 | 0,1 | 0,7 | 0,2 | 0,7 | 0,7 | NA |
| Adenin-9-yl | (S)—CH$_2$OH | 100 | 20 | 7 | 1 | 20 | 7 | 20 | 20 | 7 | 7 |
| 5-(2-Bromovinyl)-2'-deoxyuridine | | 400 | 0,02 | 0,02 | 0,02 | 4 | 1 | 10 | NA | NA | 7 |

Abbreviations:
MIC$_{50}$ lowest concentration of compound I, effecting 50% inhibition of the virus-induced cytopathic effect;
MCC$_{50}$ lowest concentration of compound I, effecting observable morphological changes in tissue culture cells not infected with the virus;
NA inactive;
HSV herpes virus;
VV vaccinia virus.

TABLE 2

| | Compounds of general formula I. | | | | | | |
| B | R | Configuration C(2) | Method$^a$ | Yield % | R$_F^b$ | k$^c$ | E$_{Up}^d$ |
|---|---|---|---|---|---|---|---|
| Uracil-1-yl | H | — | 2 | 52 | 0,26 | 0,13 | 0,82 |
| Thymin-1-yl | H | — | 2 | 45 | 0,30 | 0,22 | 0,82 |

TABLE 2-continued

Compounds of general formula I.

| B | R | Configuration C(2) | Method[a] | Yield % | $R_F$[b] | k[c] | $E_{Up}$[d] |
|---|---|---|---|---|---|---|---|
| Cytosin-1-yl | H | — | 2 | 47 | 0,27 | 0,35 | 0,70 |
| 6-Methylpurin-9-yl | H | — | 2 | 43 | 0,37 | 4,66 | 0,78 |
| Guanin-9-yl | H | — | 2 | 37 | 0,12 | 0,66 | 0,72 |
| Hypoxanthin-9-yl | H | — | 6 | 90 | 0,23 | 0,74 | 0,79 |
| Adenin-9-yl | H | — | 2 | 56 | 0,22 | 2,52 | 0,75 |
| 2-Aminoadenin-9-yl | H | — | 2 | 56 | 0,08 | 0,42 | 0,74 |
| 8-Bromoadenin-9-yl | H | — | 7 | 45 | 0,26 | 2,97 | 0,78 |
| 2-Aminopurin-9-yl | H | — | 2 | 54 | 0,37 | 0,42 | 0,75 |
| 6-Hydrazinopurin-9-yl | H | — | 2 | 37 | 0,22 | 0,76 | 0,78 |
| 7-Deaza-8-azaadenin-9-yl | H | — | 2 | 65 | 0,26 | 3,24 | 0,85 |
| 7-Deaza-8-azahypoxanthin-9-yl | H | — | 6 | 85 | 0,29 | 1,59 | 1,00 |
| Uracil-1-yl | CH$_2$OH | RS | 4 | 78 | 0,21 | 0,72 | 0,82 |
| Cycosin-1-yl | CH$_2$OH | S | 4 | 50 | 0,23 | 0,24 | 0,72 |
| 5-Methylcytosin-1-yl | CH$_2$OH | S | 4 | 66 | 0,28 | 0,35 | 0,78 |
| Thymin-1-yl | CH$_2$OH | S | 4 | 55 | 0,27 | 0,85 | 0,82 |
| 5-Fluoruracil-1-yl | CH$_2$OH | RS | 4 | 52 | 0,15 | 0,27 | 1,08 |
| Guanin-9-yl | CH$_2$OH | RS | 4 | 62 | 0,11 | 0,50 | 0,78 |
| Guanin-7-yl | CH$_2$OH | RS | 4 | 60 | 0,13 | 0,54 | 0,78 |
| Adenin-9-yl | CH$_2$OH | S | 4 | 64 | 0,22 | 2,79 | 0,75 |
| Adenin-9-yl | CH$_2$OH | RS | 8 | 65 | 0,22 | 2,79 | 0,75 |
| Adenin-3-yl | CH$_2$OH | RS | 4 | 75 | 0,22 | 1,53[e] | 0,75 |
| Hypoxanthin-9-yl | CH$_2$OH | RS | 4 | 75 | 0,28 | 0,72 | 0,80 |
| Hypoxanthin-9-yl | CH$_2$OH | S | 5 | 82 | 0,28 | 0,72 | 0,80 |
| 2-Methyladenin-9-yl | CH$_2$OH | RS | 4 | 75 | 0,27 | 1,34[f] | 0,65 |
| 2-Methylthioadenin-9-yl | CH$_2$OH | RS | 4 | 70 | 0,32 | 4,10[f] | 0,66 |
| 2-Aminoadenin-9-yl | CH$_2$OH | RS | 4 | 78 | 0,23 | 0,87 | 0,70 |
| 2-Aminoadenin-9-yl | CH$_2$OH | S | 4 | 71 | 0,08 | 0,87 | 0,62 |
| 2-Aminopurin-9-yl | CH$_2$OH | RS | 4 | 80 | 0,25 | 0,65 | 0,76 |
| N$^6$-Dimethyladenin-9-yl | CH$_2$OH | RS | 4 | 85 | 0,43 | 6,10[f] | 0,80 |
| 8-Bromoadenin-9-yl | CH$_2$OH | S | 7 | 45 | 0,26 | 5,14[g] | 0,70 |
| 8-Hydroxyadenin-9-yl | CH$_2$OH | RS | 4 | 60 | 0,18 | 1,96 | 0,87 |
| 7-Deaza-8-azaadenin-9-yl | CH$_2$OH | RS | 4 | 87 | 0,25 | — | 0,85 |
| 6-Hydroxylaminopurin-9-yl | CH$_2$OH | RS | 5 | 42 | 0,16 | 0,50 | 0,84 |
| 6-Hydrazinopurin-9-yl | CH$_2$OH | RS | 5 | 47 | 0,14 | 0,52 | 0,78 |
| 6-Thiopurin-9-yl | CH$_2$OH | RS | 4 | 60 | 0,15 | 1,18 | 1,00 |
| Purin-9-yl | CH$_2$OH | RS | 4 | 64 | 0,17 | 1,14 | 0,88 |
| Xanthin-9-yl | CH$_2$OH | RS | 6 | 72 | 0,08 | 0,46 | 1,13 |

Notes
[a]Number of the Example, describing the preparation:
[b]paper chromatography in 2-propanol - conc. aqueous ammonia - water (7:1:2);
[c]HPLC elution constant on a 200 × 4 mm RPS C18 (5μ) column in 0.05 mol · l$^{-1}$ triethylammonium hydrogen carbonate, pH 7.5, containing 5 vol % of methanol;
k = (k$_R$−k$_0$)/k$_0$, where k$_R$ is retention time of the compound in min and k$_0$ hold-up time of the column in min;
[d]electrophoretical mobility (50 V/cm) in 0.05 mol · l$^{-1}$ triethylammonium hydrogen carbonate, pH 7.5 on a paper Whatman No 3MM related to uridine 3 -phosphate;
[e]HPLC according to (c), eluent contains no methanol;
[f]HPLC according to (c), eluent contains 15 vol % of methanol;
[g]HPLC according to (c), eluent contains 7.5 vol % of methan

What we claim is:

1. A compound of the formula

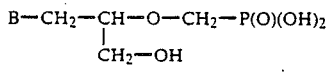

wherein B is selected from the group consisting of
uracil-1-yl,
cytosin-1-yl,
5-methylcytosin-1-yl,
thymin-1-yl,
5-fluoruracil-1-yl,
guanin-9-yl,
guanin-7-yl,
adenin-3-yl,
hypoxanthin-9-yl,
2-methyladenin-9-yl,
2-methylthioadenin-9-yl,
2-aminoadenin-9-yl,
2-aminopurin-9-yl,
N$^6$-dimethyladenin-9-yl,
8-bromoadenin-9-yl,
8-hydroxyadenin-9-yl,
6-hydroxylaminopurin-9-yl,
6-hydrazinopurin-9-yl,
6-thiopurin-9-yl,
purin-9-yl, and
xanthin-9-yl.

2. The compound of claim 1, wherein B is selected from the group consisting of uracil-1-yl, cytosin-1-yl, 5-methylcytosin-1-yl, thymin-1-yl, and 5-fluorouracil-1-yl.

3. The compound of claim 2, wherein B is cytosin-1-yl.

UNITED STATES PATENT AND TRADEMARK OFFICE

CERTIFICATE EXTENDING PATENT TERM
UNDER 35 U.S.C. § 156

PATENT NO.      :   5,142,051

ISSUED          :   August 25, 1992

INVENTOR(S)     :   Antonin Holy et al.

PATENT OWNERS   :   Institute of Organic Chemistry and Biochemistry of the Academy of Sciences of the Czech Republic and Rega Institut PRODUCT         :   VISTIDE™ (cidofovir)

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 305 days from August 25, 2009, the original expiration date of the patent, subject to the provisions of 35 U.S.C. § 41(b), with all rights pertaining thereto as provided by 35 U.S.C. § 156(b).

I have caused the seal of the Patent and Trademark Office to be affixed this 23rd day of October 1998.

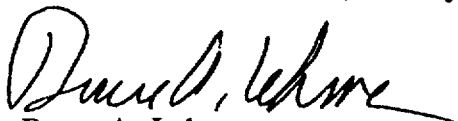

Bruce A. Lehman
Assistant Secretary of Commerce and
Commissioner of Patents and Trademarks